United States Patent
Schoeniger et al.

(10) Patent No.: US 6,960,285 B2
(45) Date of Patent: Nov. 1, 2005

(54) ELECTROKINETICALLY PUMPED HIGH PRESSURE SPRAYS

(75) Inventors: Joseph S. Schoeniger, Oakland, CA (US); Phillip H. Paul, Livermore, CA (US); Luke Schoeniger, Pittsford, NY (US)

(73) Assignee: Sandia Naitonal Laboratories, Livermore, CA (US)

(*) Notice: Subject to any disclaimer, the term of this patent is extended or adjusted under 35 U.S.C. 154(b) by 570 days.

(21) Appl. No.: 10/260,164

(22) Filed: Sep. 30, 2002

(65) Prior Publication Data

US 2003/0038027 A1 Feb. 27, 2003

Related U.S. Application Data

(62) Division of application No. 09/595,799, filed on Jun. 16, 2000, now Pat. No. 6,495,015.
(60) Provisional application No. 60/140,100, filed on Jun. 18, 1999, now abandoned.

(51) Int. Cl.$^7$ .............................. B05B 5/00; A61F 13/00
(52) U.S. Cl. ....................... 204/450; 204/454; 204/600; 204/601; 604/21; 607/2
(58) Field of Search ................................ 204/450, 454, 204/600, 601; 604/21; 607/2

(56) References Cited

U.S. PATENT DOCUMENTS

| 6,013,164 A | 1/2000 | Paul et al. |
| 6,029,889 A | 2/2000 | Paul et al. |
| 6,410,046 B1 * | 6/2002 | Lerner ......................... 424/434 |
| 6,572,749 B1 * | 6/2003 | Paul et al. .................. 204/450 |

OTHER PUBLICATIONS

Paul, P.H.; Arnold, D.W.; Rakestraw, D.J.; "Electrokinetic generation of high pressures using porous microstructures," MicroTotal Analysis '98, D.J. Harrison & A. van den Berg eds.; Kluwer Academic Publishers, London, 1998, pp. 49–52.

* cited by examiner

Primary Examiner—Arun S. Phasge
(74) Attorney, Agent, or Firm—Donald A. Nissen

(57) ABSTRACT

An electrokinetic pump capable of producing high pressure is combined with a nozzle having a submicron orifice to provide a high pressure spray device. Because of its small size, the device can be contained within medical devices such as an endoscope for delivering biological materials such as DNA, chemo therapeutic agents, or vaccines to tissues and cells.

5 Claims, 3 Drawing Sheets

ELECTROKINETICALLY PUMPED HIGH PRESSURE SPRAYS

CROSS REFERENCE TO RELATED APPLICATIONS

This application is a division of prior U.S. patent application Ser. No. 09/595,799 originally filed Jun. 16, 2000 entitled "ELECTROKINETICALLY PUMPED HIGH PRESSURE SPRAYS," now U.S. Pat. No. 6,495,015 and claims benefit to prior U.S. Provisional Application Ser. No. 60/140,100 filed Jun. 18, 1999, from which priority is claimed.

STATEMENT OF GOVERNMENT INTEREST

This invention was made with Government support under government contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

BACKGROUND OF THE INVENTION

The present invention is directed generally to a device that combines a miniaturizable high pressure pumping means and nozzle for generating a high pressure spray and particularly to a device for injecting DNA, chemo-therapeutic agents, and vaccines into cells and tissues. Because of its small size the device can be incorporated into an endoscope or catheter, thereby providing non-invasive access to difficult to reach tissues, such as intestinal epithelium or the left ventricle interior wall, for therapy.

There is, at present, a great deal of interest in the medical technologies and biotechnology in applications that allow the insertion of genes into live eukaryotic cells and tissues. Two new areas of medical research, gene therapy, and DNA vaccines, that may have revolutionary impact of the practice of medicine, depend on such gene insertion techniques.

A surprisingly successful method for the introduction of DNA into cells has been the physical bombardment of cells and tissues with high-speed droplets or particles carrying DNA as discussed in Yang, N. S., and Sun, W. H., *Nature Medicine*, 1, 481–483, 1995; Johnston, S. A. and Tang, D. C., *Methods in Cell Biology*, 43, 353–365, 1994; Fynan, E. F. et al., *Proceedings of the National Academy of Sciences of the United States of America*, 11478–11482, 1993. In the first implementation of this technique (Sanford, J. C. et al., *Part. Sci, Technol.*, 5, 27–37, 1987) the DNA was literally shot through the walls of the target cells. Although initially developed for use in plant cell lines, this approach has been found to result in significant levels of incorporation and expression of the DNA in a wide range of targets, including mammalian cells in culture, intact rat liver, and skin. The success of the strategy is surprising, not in the least, because it requires that cells remain viable after having submicron-size holes torn in their membranes, although it is not clear whether DNA must be ballistically transported into the cells, or simply the cells permeabilized to allow DNA on or around the cells to diffuse or be transported in. Other (seemingly more controlled) techniques for introducing DNA that are successful in vitro, such as single-cell microinjection, and electroporation, are not easily adaptable for clinical in situ gene therapy. Techniques that rely on vectors such as viruses or liposomes to deliver DNA to target tissues have other limitations, such as the need to find a vector that will target a certain tissue or cell type and will be specific to that cell type. If such vectors are injected, the region of transfected cells is not spatially localized (except by means of biological specificity). Bombardment methods have the advantage that they allow DNA to be introduced without the need for packing it in a vector, and the DNA can then be aimed (quite literally) at accessible target cells, though it is also possible to shoot viral particles into cells.

One effective means for DNA bombardment of cells is the use of a shock tube. In one example of such an instrument (Nabulsi, S. M., et al., *Measurement Sci. and Tech.*, 5, 267–274, 1994), a membrane, located at the entrance of the tube, is ruptured by a high pressure gas to create a shock wave that impinges upon a secondary membrane at the other end of the tube. This secondary membrane is coated with DNA-containing particles, such as DNA adsorbed onto gold beads. When the shock wave hits it, the particles are accelerated to supersonic velocities and embed themselves in the target cells or tissues. Another simpler method is the use of a traditional jet injector (Haensler, J., et al., *Vaccine*, 17, 628–638, 1999), which consists in its most basic form of a spring-loaded plunger in a cylinder barrel with a small-aperture nozzle. When the plunger is suddenly released, the cylinder acts as a hydraulic intensifier, and a high pressure (e.g., 10 MPa) stream is emitted from the nozzle with velocities on the order of 140 m/sec. There is an apparent predominance of shock-tube or similar gas-driven methods in the scientific literature, probably related to their demonstrated efficacy for a variety of applications. This may in turn be due to the higher particle velocities that are achieved, allowing more cells to be permeated and deeper penetration into tissues and easier delivery of DNA through liquid layers and dead cells.

There is a long history of the use of jet injectors for intra-/subcutaneous vaccinations (Hingston, R. A. and Hughes, J. G., *Anesth. Analg. Cleve*., 221–242, 1947). They are familiar, in some variant, to much of the population from their use in mass immunization programs. Shock-tube-based methods may also be used on skin as the target organ, or on surgically exposed tissues, as mentioned above. However, it is not straightforward to create a shock tube or high pressure gas feed system that can be safely used inside a body cavity or the cardiovascular system, and this factor limits the applicability of these strategies for introducing DNA into diseased tissues. Aside from the obvious pressure safety concerns, shock-tube methods would be precluded in the cardiovascular system, where any gas release would be unacceptable. More fundamentally, miniaturization of jet and shock-based designs is problematical because of simple hydrodynamic scaling issues. For example, to maximize nozzle velocities of jet injections, is it desirable to have a large diameter cylinders in order to minimize O-ring frictional losses and pressure drop in the barrel. For constant nozzle velocity, these losses increase as the inverse square of the barrel radius, and gas flows in small diameter tubes have similar problems.

Consideration of the above discussion leads to several design features that should be met by a miniaturized DNA delivery device for internal use, in addition to demonstrated efficacy for performing DNA transfer:

1) The principle of operation should be such that performance does not deteriorate as the device is miniaturized, and the device should fit in the endoscope lumen (approximately 0.5 cm in diameter).
2) No high pressure gas supply lines that would have to run along the endoscope.
3) Only physiologically compatible fluids or particles released, with no release of gases.

4) Injection velocities should be substantially higher than that of jet injectors.
5) Power must be supplied by small wires that could be fit into an endoscope or catheter.
6) The device must be sterilizable
7) The device should allow arrays of nozzles to be used.
8) The device should be able to be manufactured as a disposable item.

SUMMARY OF THE INVENTION

The present invention makes use of miniature high pressure pump technology combined with a nozzle having a sub-micron aperture or orifice to provide a novel device for delivering high pressure sprays at low flow rates, generally, and for direct gene/DNA delivery into cells that is suitable for clinical use on the end of an endoscope or catheter, in particular. Thus, in contrast to prior art devices for introduction of DNA into cells, the present device provides for direct genetic manipulation of difficult to access tissues, such as intestinal epithelium or the left ventricular wall, through relatively non-invasive means and thus, enhances the ability to address diseases of major importance such as heart disease and cancer of the alimentary tract. Further, the novel device disclosed herein is also generally useful for microinjection of chemo-therapeutic agents or vaccines into skin and other tissue. Furthermore, the inventive device has no moving parts, is constructed of simple materials, is compatible with micromachining such that inexpensive mass production is possible, releases only very small amounts of gas, provides injection velocities substantially higher than prior art devices such as jet injectors, and is sterilizable.

Generally, the inventive device integrates a high pressure electrokinetic pump (EKP) with a micro-nozzle, i.e., a nozzle having an aperture or orifice whose opening is sub-micron in diameter, for the delivery of a high pressure, low flow rate spray, including delivery of DNA or other biological materials into tissues. It has been demonstrated that the EKP is capable of providing levels of very high pressure ($>10^4$ psi or 100 Mpa) at low flow rates. Thus, the present device can evolve higher pressures than prior art spring-actuated devices or even shock tubes. Moreover, by using an EKP for pressure generation, the need for high pressure lines is obviated and thus the pressure losses that are encountered in prior art devices that transport hydraulic power from the pressure generator to the point of use are eliminated.

DETAILED DESCRIPTION OF THE INVENTION

Figure 1:
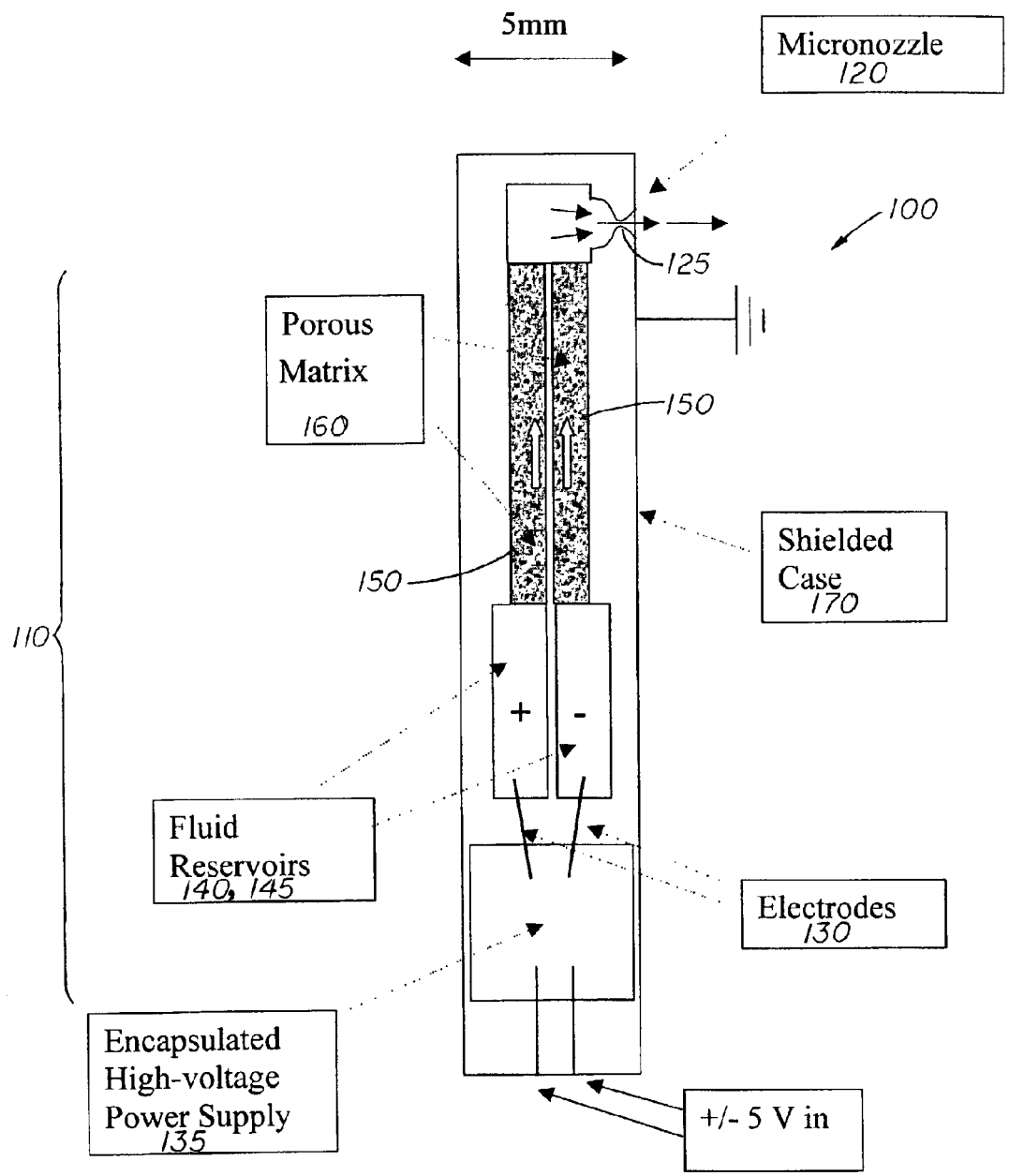
FIG. 1 shows an embodiment of the present invention.
Figure 2:
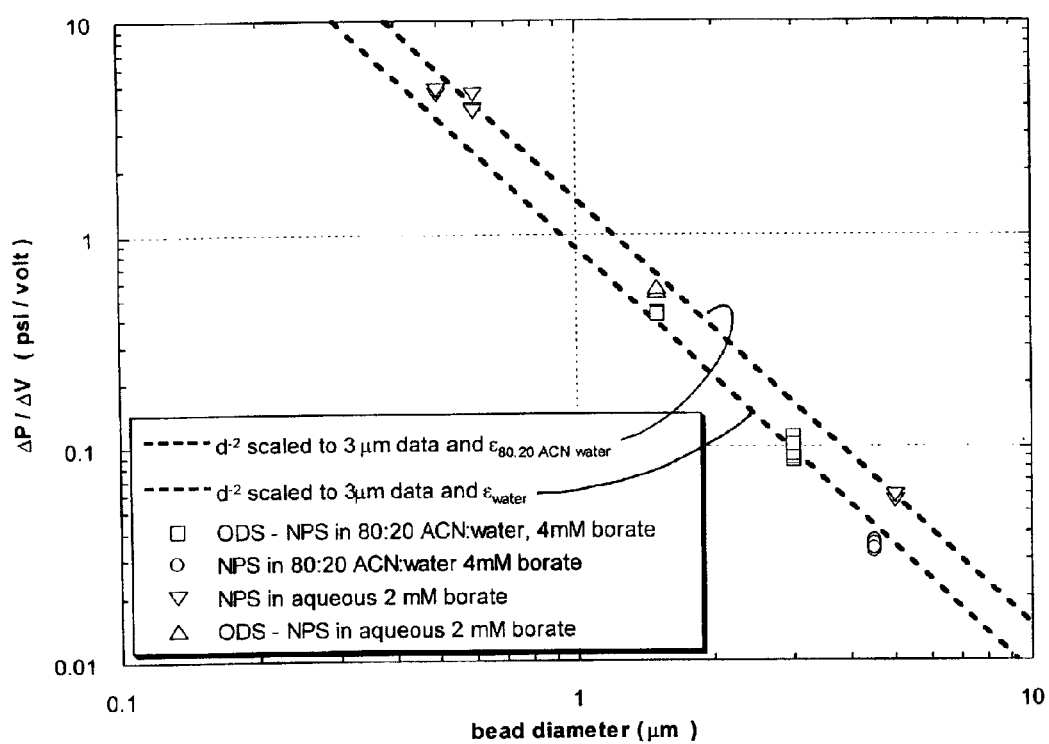
FIG. 2, is a plot of the pressure developed as a function of pore size of the porous dielectric pump medium.
Figure 3:
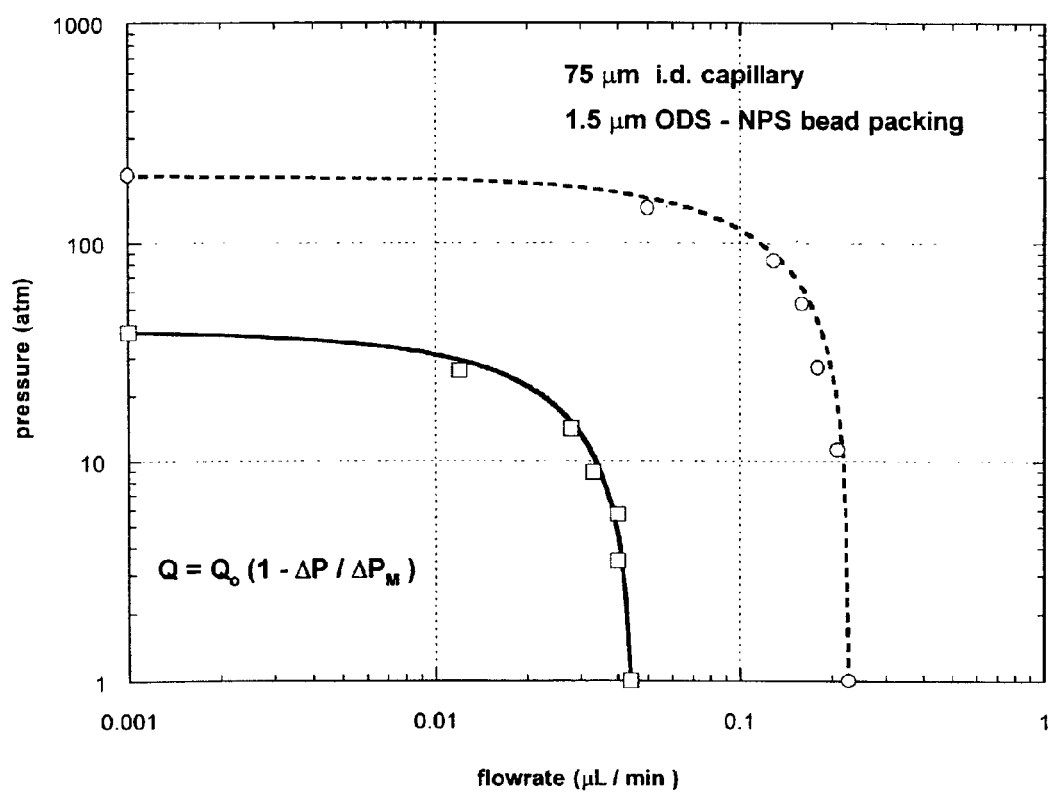
FIG. 3 compares the experimentally derived values of flowrate as a function of back-pressure with calculated values.

The present invention is directed to a device that integrates a high pressure electrokinetic pump (EKP) with a micro-nozzle for the delivery of a high pressure, low flow rate spray, including delivery of DNA or other biological materials into tissues. Because of its small size the device can be incorporated into an endoscope or catheter, thereby providing non-invasive access to difficult to reach tissues, such as intestinal epithelium or the left ventricle interior wall, for therapy.

In order to understand the invention better a brief description of the operation of an electrokinetic pump (EKP) is presented.

It has been demonstrated that it is possible to convert electric potential to hydrodynamic force and, by means of a process called electrokinetic pumping, to produce hydraulic pressures at least as great as 10,000 psi. The electrokinetic pump or EKP, comprises at least one tube or flow channel, that can be a capillary or micro-fabricated channel, forming a fluid passageway, i.e., a microchannel. The flow channel has a porous dielectric material disposed therein and contains an electrolyte in contact with one or more pairs of spaced electrodes. The porous dielectric medium can include small particles: high surface area structures, fabricated within the microchannel, and porous materials, such as porous organic polymer materials. An electric potential can be applied to the electrodes by means of a conventional high voltage power supply or batteries and the electric potential can assume various forms suitable to the operation of the system described herein, such as having a varying amplitude, shape, and period.

It is known in the art that solid materials that display a negative surface charge (e.g. silica at pH 4 or greater) will produce a flow of the liquid from the positive toward the negative terminal of the applied potential. Whereas solid materials that display a positive wall charge (e.g. alumina at pH 7 or less) will produce a flow from the negative toward the positive terminal of the applied potential. It is also known in the art that the surface of a solid material can be chemically altered to change the sign of the surface charge (e.g. A quaternary amine can be grafted onto a silica material to switch the natural surface charge from negative to positive). By connecting two electrokinetic pumps in series (one having a positive and the other a negative surface charge) a pressure is generated at the common junction by applying a potential across the whole device. Flow is thus toward the common junction from the two reservoirs at the open ends of the two electrokinetic pumps. In this fashion no electrode connection is required at the common junction, and therefore, there is no generation of electrolysis products at the common junction. Further, by utilizing a floating power supply, the common junction can be held at an arbitrary common mode potential, preferably an earth ground potential.

The foregoing is intended as only a brief overview of a description for how a pair of electrokinetic pumps might be assembled to work together in tandem as a "T" pump. A more thorough description of this apparatus is provided in co-pending U.S. patent application Ser. No. 09/336,535 entitled "Method for Eliminating Gas Blocking in Electrokinetic Pumping Systems" by Arnold, Paul and Schoeniger filed Jun. 18, 1999, the disclosure of which is herein incorporated by reference and made part of the disclosure of the present invention.

The electrolyte, which is in contact with the spaced electrodes, can be an aqueous, or an organic liquid or mixtures thereof and can comprise the constituents of the spray. The electric field applied across the EKP by the spaced electrodes will cause the electrolyte contained in the porous dielectric medium to flow and, when presented with an external flow resistance can create pressures of thousands of psi at the down stream end of the EKP. The flowrate of the electrolyte is proportional to the magnitude of the applied electric field (V/m applied across the EKP) and the pressure generated is proportional to the voltage across the device. The direction of flow of the electrolyte is determined by both the nature of the electrochemical interaction between the porous dielectric medium and the electrolyte, and the polarity of the applied electric potential. A detailed discussion of the theory and operation of the electrokinetic pumping process can be found in U.S. Pat. Nos. 6,013,164 and 6,029,882 both entitled ELECTROKINETIC HIGH PRESSURE HYDRAULIC SYSTEM, issued respectively, on Jan. 11 and Feb. 1, 2000 to Paul and Rakestraw, and incorporated herein by reference.

FIG. 1 schematically illustrates one embodiment in accordance with the present invention. The miniature high pressure spray device 100 generally comprises an electrokinetic pump 110 and micro-nozzle 120, having an aperture 125 whose diameter is in the sub-micron range. Electrokinetic pump 110 typically comprises a pair of electrodes 130, a power supply means 135 for providing electric power to the electrodes, flow channels 150, having a porous dielectric pump medium 160 disposed therein, and fluid reservoirs 140 and 145, each containing an electrolyte as well as one of electrodes 130, disposed at the inlet end of flow channels 150. The whole assembly is contained in a shielded case 170. The entire device can be made of heat-stable porous ceramics or polymers, so that it is heat sterilizable.

It will be appreciated, that for some applications it can be desirable to produce a spray by means of a pressure pulse. In those instances, a membrane (not shown) or similar device, designed to rupture at a given pressure, can be placed between the outlet end of flow channels 150 and the aperture 125 of nozzle 120.

Because the EKP is based on physical phenomena that operate at the microscale, and has no moving parts, it can be easily miniaturized and have a variety of formats. FIG. 1 shows a miniature cylindrical device that would fit in the open bore in the center of an endoscope. The inventors have shown that high pressure EKPs pumping structures can be made out of packed capillaries that are sub-millimeter in external diameter, thus designs that fit into a bore of a few millimeters, are contemplated and it should be possible to make designs that are smaller in diameter for use in catheters. FIG. 1 indicates that a miniature high-voltage power supply would be encapsulated in the device, but this should be understood as only one possible configuration. Currently available modular high voltage power (i.e. 3 kV) supplies come as ~1 cm cubes, and could be fabricated to fit within the device, but it is also straightforward to run insulated high voltage wires down the length of the endoscope, with a small external power supply at the head of the endoscope. The volume of electrolysis gases produced is minimal, and they can be vented to the room though the bore if necessary, as they are generated in reservoirs at the low pressure end of the pump.

While the embodiment illustrated in FIG. 1 is shown with one nozzle disposed at the outlet end of flow channels 150, it is contemplated that an array of nozzles could be similarly disposed.

The physical principles behind electrokinetic pumping are well established. However previous experimental attempts to realize the theoretical predictions achieved only modest pressures (e.g. less than a few psi) and observed that the pressure did not scale linearly with the total applied voltage. Some unknown nonlinear process is now believed to have limited the ability of electroosmotic flow to achieve high pressures. It has been shown in the references above, that EKP pressure scales linearly with total applied voltage and pressures in excess of 9000 psi can be achieved. The present 'upper limit' is due to mechanical failure of the test apparatus rather than any limiting physical process in electrokinetic pressure generation. The theoretical scaling for both pressure and flowrate have been experimentally confirmed.

One key advantage of the EKP technology is the capability to generate high pressure liquid flow in a compact and efficient device. In a miniature device the intrinsic strength of common materials is sufficient to safely contain these pressures. Even though the pressure is high, the surface area hence the forces are small. A second key advantage is that pressure can be generated at the point of use. This obviates any need for high pressure lines and minimizes the pressure losses that normally occur in transporting the hydraulic power from the pressure generator to the point of use.

It is estimated that liquid flow rates of order 0.1 $\mu$liter/min., or greater, will be required to achieve useful mass transfer rates particularly for endoscopic gene therapy. For a working fluid of water at 10,000 psi and taking into account the finite compressibility, this translates to an orifice diameter of 0.15 microns and a nozzle throat velocity in excess of 400 m/sec. For a short, rapidly converging nozzle, standard engineering correlations suggest that less than 10% of the pressure head will be lost in the nozzle. The micro-nozzles can be fabricated using laser machining of glass, sapphire, or ceramic materials.

Little is know about the generation of particles from a very high pressure liquid jet as issuing through a sub-micron diameter orifice. It is thought that the nozzle flow will be laminar, however with the decompression and the supersonic velocity, the jet will be highly unstable and is expected to break-up immediately into a mixture of very fine droplets and vapor. The kinetic energy in the jet is well above the energy required to overcome the surface tension and form particles of sizes less than one micron in diameter.

Based on our measurements, a voltage on the order of 3 kV and an EKP with an inside diameter on the order of 0.15 mm is required to achieve a pressure on the order of 10,000 psi at the desired flow rate. FIG. 2 shows experimental results for EKPs using packed spherical particles as the porous material. These results confirm the prediction that pressure generated should go inversely with the square of the pore diameter (which is directly proportional to the bead diameter). FIG. 3 shows experimental results for flowrate as a function of back-pressure again confirming the predicted behavior (shown in the solid curves).

For shock-tube-based introduction of DNA into cells, the DNA is typically adsorbed onto gold beads, and the gold beads are the actual projectiles that carry the DNA into the cell layers. Therefore, entraining DNA-containing particles in the jet produced by the EKP, rather than relying on the droplets, is contemplated. This can allow greater penetration depths to be achieved, because of the greater stability (e.g., no evaporation) of the gold, and its greater density. Also, adsorbing the DNA onto a solid support may reduce DNA scission. DNA can also be adsorbed on spermidine-coated gold particles, and gold particles are available in a range of sizes down to a few nanometers (colloidal gold). These particles can be entrained either by filling the pump chamber with a suspension prior to pressurization, or, if the particles are small enough to pass through the pump matrix's pores, simply pump the suspension as the primary liquid. Further, the use of fluorescent nanoparticles as the entrained vehicle is also contemplated.

Safety Issues

Although high voltages are used, currents are in the micro-Ampere range, so only milliwatt power consumption occurs. We note that it is now fairly routine for patients to have permanently implanted automatic defibrillators, devices that have, by definition, high voltages with potentially lethal (i.e., heart stopping) amounts of stored energy. As there has been little problem with accidental electrocution with these devices, it seems likely that the high voltage system needed here for a temporary procedure could be designed safely. Electrically balanced pump designs can be implemented that do not produce electrical fields at the nozzle aperture. As additional protection, it is easy to provide an external sensing lead to shutoff the voltage if any current is detected at the nozzle aperture. Due to the small volumes, the stored hydraulic energy is minimal, and as are the pressure hazards.

We claim:

1. A device for delivering a material directly into cells and tissues, comprising:
    a) an electrokinetic pump, comprising;
        a pump inlet and a pump outlet;
        at least two microchannels, wherein each of said microchannels include a fluid inlet, a fluid outlet, and a porous dielectric material disposed within said microchannel, said microchannels connected in pairs at one end to form a common junction, said common junction in fluid communication with said pump outlet, said porous dielectric material contained within each microchannel of each pair of microchannels having a different Zeta potential;
        an electrolyte disposed throughout said porous dielectric material;
        a fluid reservoir disposed at each of said microchannel inlets, said fluid reservoirs containing said electrolyte such that each said fluid reservoir is in fluid communication with said porous dielectric material within said microchannel to which said reservoir is disposed;
        electrode means contained within each of said fluid reservoirs; and
        means for applying an electric potential to each of said electrode means;
    b) at least one nozzle disposed at said outlet of said electrokinetic pump, said nozzle having an orifice; and
    c) a shielded case for containing at least said electrokinetic pump and said nozzle, said case for fitting within an endoscope.

2. The device of claim 1, wherein the case is made from porous ceramics or heat sterilizable polymers.

3. The device of claim 1, wherein the delivered material comprises said electrolyte.

4. The device of claim 3, wherein said delivered material further includes one or more materials selected from the group consisting of any active or inert carrier agent or diluent, DNA or DNA fragments, chemo-therapeutic agents, vaccines, drugs, and any combinations thereof.

5. A method for delivering a material directly into cells and tissues, comprising:
    a) providing a high pressure spray device, comprising:
        i) an electrokinetic pump, comprising:
            a pump inlet and a pump outlet;
            at least two microchannels, wherein each of said microchannels include a fluid inlet, a fluid outlet, and a porous dielectric material disposed within said microchannel, said microchannels connected in pairs at one end to form a common junction, said common junction in fluid communication with said pump outlet, said porous dielectric material contained within each microchannel of each pair of microchannels having different dielectric properties;
            an electrolyte disposed throughout said porous dielectric material;
            a fluid reservoir disposed at each of said microchannel inlets, said fluid reservoirs containing said electrolyte such that each said fluid reservoir is in fluid communication with said porous dielectric material within said microchannel to which said reservoir is disposed;
            electrode means contained within each of said fluid reservoirs; and
            means for applying an electric potential to each of said electrode means;
        ii) providing at least one nozzle disposed at said outlet of said electrokinetic pump, said nozzle having an orifice; and
        iii) providing a shielded case for containing at least said electrokinetic pump and said nozzle, said case for fitting within an endoscope; and
    b) incorporating said material into said electrolyte such that said spray produced entrains said material.

* * * * *